United States Patent [19]

Leclerc et al.

[11] Patent Number: 5,336,880
[45] Date of Patent: Aug. 9, 1994

[54] PROCESS FOR THE CORRECTION OF DISTORTIONS IN RADIOLOGICAL IMAGES

[75] Inventors: Vincent Leclerc; Catherine Picard, both of Paris; Blandine Lavayssiere, Ville d'Avray, all of France

[73] Assignee: General Electric CGR S.A., Issy les Moulineaux, France

[21] Appl. No.: 793,351

[22] PCT Filed: Jul. 13, 1989

[86] PCT No.: PCT/FR89/00375

§ 371 Date: Jan. 13, 1992

§ 102(e) Date: Jan. 13, 1992

[87] PCT Pub. No.: WO91/01071

PCT Pub. Date: Jan. 24, 1991

[51] Int. Cl.$^5$ .............................................. H01J 40/14
[52] U.S. Cl. ................................... 250/214 VT; 378/207
[58] Field of Search ................. 250/214 VT; 378/207, 378/99, 7

[56] References Cited

U.S. PATENT DOCUMENTS

| | | |
|---|---|---|
| 4,736,399 | 4/1988 | Okazaki . |
| 4,837,796 | 6/1989 | Ema ........................ 378/7 |
| 4,872,187 | 10/1989 | Nakahata et al. ................ 378/4 |
| 5,191,621 | 3/1993 | Brok ........................... 378/207 |
| 5,235,528 | 8/1993 | Silver et al. ................. 378/7 |

FOREIGN PATENT DOCUMENTS

| | | |
|---|---|---|
| 0021366 | 1/1981 | European Pat. Off. . |
| 0293293 | 11/1988 | European Pat. Off. . |
| 3419043 | 11/1985 | Fed. Rep. of Germany . |

OTHER PUBLICATIONS

Proceedings of 1986 IEEE International Conference on Robotics and Automation, Apr. 7–10, 1986, San Francisco (Calif., US), vol. 1, IEEE, N. Yokobori et al.: "Sub-pixel geometric correction of pictures by calibration and decalibration" pp. 448–453.

*Primary Examiner*—David C. Nelms
*Attorney, Agent, or Firm*—Nilles & Nilles

[57] ABSTRACT

Process to correct distortion of radiological images by obtaining the image of a regular test chart and assessing the distortions to which the image is subjected. This assessment is used to correct normal images obtained with the installation. One obtains automatically the distortion corrections to be applied to the image elements by eliminating (55) the image background by creating (63) images of similar columns, by labelling (66) the columns detected and by calculating (71) the co-ordinates of the intersections of these columns. The calculation of the intersection co-ordinates is improved by replacing (89) these columns by straight segments whose position is calculated by a regression of least error squares over all the image elements belonging to this column and situated near this intersection. Preferably, all these calculations should be made through implementing mathematical morphology operations.

20 Claims, 5 Drawing Sheets

PROCESS FOR THE CORRECTION OF DISTORTIONS IN RADIOLOGICAL IMAGES

BACKGROUND OF THE INVENTION

An object of the present invention is a process for the correction of the distortion of radiological images acquired with a luminance intensifier tube. It can be applied more particularly to the medical field. It can be implemented either in direct radioscopy or in radiology with digitized processing of the signal representing the image. It relates more particularly to future-generation tomodensitometers in which the detection element will be a luminance intensifier device such as this. Its object is to resolve the problems of morphometry raised by the use of such tubes.

An intensifier tube of radiological images is designed to receive a low-power X-radiation and to convert this X-radiation into a more powerful light radiation that can be more easily detected by a display means, especially by a camera. The reason for the weakness of the X-radiation received must be sought in the need to provide protection, especially in medicine, for patients subjected to examinations with radiation of this kind. This is so especially when such examinations are lengthy, as is the case with tomodensitometry processing operations or processing with digitization of image information elements.

An image intensifier tube essentially has a conversion panel to convert a received X-radiation into a light radiation that is capable of striking a photocathode placed in a position where it faces this panel. The conversion of X-radiation into light radiation is obtained in a known way by providing the panel with caesium iodide crystals. Under the effect of the X-ray illumination, photoelectrons are liberated from the photocathode and move towards the screen. This movement towards the screen is subjected to the effects of an electronic optical system. This electronic optical system tends towards an effect where the impacts of the photo-electrons on the screen correspond to the places on the photo-cathode from which they have been emitted.

The screen is itself of a special type: it re-emits a light image representing the electronic image conveyed by the electrons, and this image itself represents the X-ray image. This light image can then be displayed by any display means, especially a standard camera, so as to be displayed on a display device, especially a device of the television monitor type.

A display system such as this has a major drawback: the revealed image is an image that is geometrically distorted in relation to the X-ray image from which it has originated. This distortion occurs essentially between the photo-cathode, excited by the photons emerging from the conversion panel, and the screen that receives the electron radiation emitted by this photo-cathode. Indeed, during their journey, the photo-electrons are subjected to disturbing effects, notably magnetic effects, due to the earth's magnetic field. If all the photo-electrons were to be affected, during this journey, by one and the same type of disturbance, then correcting the effect of these disturbances at any part of the sequence of images to would be enough to avert problems. Unfortunately, these photo-electrons are highly sensitive to disturbances. And the inhomogeneity of the magnetic field in the places through which they pass is then such as to result in a distortion in the electronic image projected on the screen.

To give a more concrete explanation of the effects of a distortion such as this, it may be said that the image of a straight line interposed between an X-ray tube and an image intensifier such as this will be a straight line in the X-ray image that excites the panel, it will be a straight line in the photon image that strikes the photo-cathode, and it will be a straight line in the electron image that leaves this photo-cathode, but it will no longer be a straight line in the electronic image that gets displayed on the screen. Consequently, it can no longer be a straight line in the light image produced by this screen. The display device placed downline then reveals, so to speak, the result of the distortion due to the non-homogeneity of the earth's magnetic field in the space crossed by the electronic image.

Until now, it has been possible to overlook this type of drawback because the images to be produced have been essentially qualitative and because their quantitative content, namely the exactness of the drawing of the contours of the object revealed, has been a matter of little concern. However, at present, with the development of techniques, it is increasingly being sought to use these images quantitatively. For example, prosthetic fixtures may have to be made from the images obtained. In this case, it would be intolerable to have warped images. Besides, in industrial checking, this type of defect obviates any easy use of image intensifiers such as these in metrology.

Among the deformations or distortions of the image, attention may be drawn to the so-called "pincushion" distortion that arises out of the geometry of the spherical dome of the input face of the tube, namely the upper face of the panel. Attention may also be drawn to the so-called "S" deformation arising out of the deflection of the electronic paths by the magnetic fields, especially the earth's magnetic field. The distortion therefore shows a permanent component, related to a given tube, and a variable component related to the very position of the tube in the earth's magnetic field.

Various processes have been envisaged to reduce the effects of this latter distortion. A first approach, through technological developments, has tried to reduce the effects of distortion, namely the effects of the disturbing magnetic fields. To this end, the image intensifier tubes have been provided with magnetic cladding parts (elements to canalize the magnetic field) that encase the tube. However, this casing cannot cover the conversion panel, and accordingly, disturbing magnetic effects are nevertheless exerted in the vicinity of this panel at the position where they are ultimately the most effective owing to the fact that the photo-electrons liberated from the photo-cathode are moved at very low speeds in the vicinity of this panel.

To complete this device, a process has furthermore been devised wherein a coil for the production of a compensating magnetic field is positioned in the vicinity of the upper face of the tube. A French patent application No. 88 04071, filed on 29 Mar., 1988 has even envisaged the servo-linking of the current flowing through this coil to a measurement of the magnetic field to be compensated for. Despite all its promise, this process gives but imperfect results. The precision of the correction of distortion is insufficient in relation to the applications envisaged, for it too cannot be used to eliminate the "pincushion" effect.

Another process of correction of the distortions has been envisaged. It relates to a parametrical approach. According to this approach, the deformations are modelized on the basis of the knowledge of the geometrical and electro-optical characteristics of the system. This success of this process is conditioned by the precision with which the system to be modelized is known. As an analytical approach, it calls for major simplifications of the model in order to be capable of being computed. These simplifications are such that, ultimately, this process can no longer take account of every phenomenon, especially more complex phenomena resulting from the "S" deformation.

OBJECTS AND SUMMARY OF THE INVENTION

An object of the invention is to remedy these drawbacks by proposing a novel process wherein there is carried out the acquisition of images of a calibrated test chart and wherein the distortion of the image of this test chart is measured in relation to its expected theoretical shape. This measurement is naturally done for all the useful positions in space of the image intensifier tube/X-ray tube assembly. Subsequently, the radiological images acquired are corrected as a function of the assessments of this distortion. This pragmatic and non-parametrical process can be used to take account of all the physical phenomena coming into play in the distortion, as opposed to the known processes where in one way (rough technology) or another (approximate model-building), all the distortions were not taken into account.

An object of the invention, therefore, is a process for the correction of the distortion of radiological images acquired with a luminance intensifier tube, these images comprising a collection of addresses of image elements in relation with grey levels assigned to these elements, wherein:

the image of a test chart placed on the input face of this tube is acquired;
an assessment is made of the distortion of this test chart with respect to its expected theoretical shape;
and normal radiological images are corrected as a function of this assessment.

In one improvement, the acquisition of the real image of a test chart, given the multiplicity of the possible positions in space of the intensifier tube/X-ray tube assembly, is automatic. Furthermore, this acquisition is done by using a particular test chart, the structure of which is such that it does not itself introduce imprecision into the correction computations that are to be deduced from it.

The invention is used especially in systems of digital angiography, where it is desirable to estimate the geometrical deformations in order to correct the measurements of distance, areas or volumes made on the organs from the images, but in which it is also valuable to be able to effectively restore the images. This restoring is useful in the arteriography of the lower limbs, when it is sought to reconstruct a leg from several juxtaposed images for example.

In generalized tomodensitometry, in the case of 3D reconstruction using 2D projections, the correction of the distortions is indispensable and calls for high precision. The precision comes into play at two instants: during the calibration of the acquisition systems and during the restoring of the images proper, prior to any 3D reconstruction. It could be shown that the requisite levels of precision can be obtained with the invention: i.e. precision of 1/10th of an image element for the calibration of the acquisition system, and ½ of an image element for the 3D reconstruction from 2D projections. Furthermore, it is possible to be satisfied with corrections of the order of one pixel for geometrical measurements on the image.

BRIEF DESCRIPTION OF THE DRAWINGS

The invention will be understood more clearly from the following description and from the appended figures. These figures are given purely by way of an indication and in no way restrict the scope of the invention. In these figures.

DETAILED DESCRIPTION OF THE PREFERRED EMBODIMENTS

Figure 1:
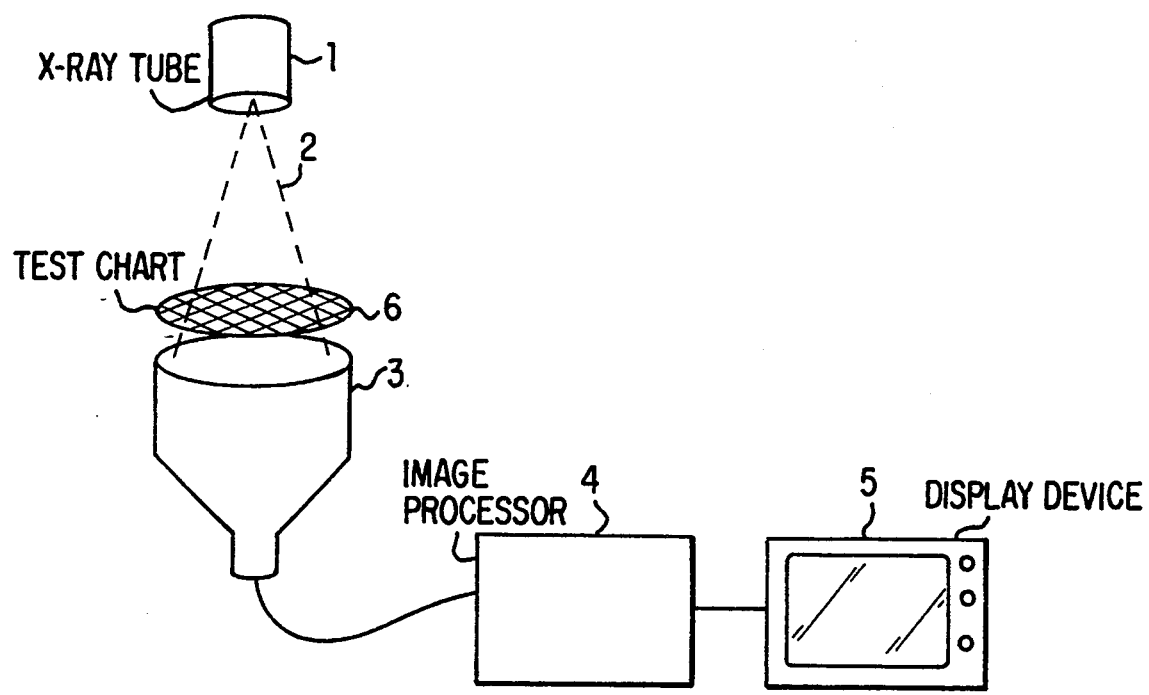
FIG. 1 shows the schematic drawing of a radiological system to implement the process of the invention.
Figure 2:
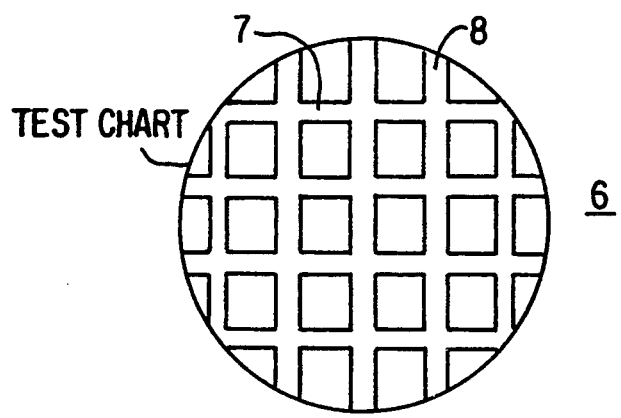
FIG. 2 shows the drawing of a standard grid that can be used as a test chart.

FIG. 1 gives a schematic view of an imaging system that can be used to implement the process of the invention. In this system, an X-ray tube 1 emits an X-radiation tube 2 towards an image intensifier tube 3. The image intensifier tube 3 is connected to an image processing device 4, which is itself connected to a device 5 for the display of the processed images. The reading of the distortions undergone by the images for a given position of the X-ray tube 1/image intensifier tube 3 assembly is given by the interposition, prior to any measurement for standard use of a test chart 6 between this tube 1 and the intensifier 3. Preferably, the test chart 6 has substantially the same dimensions as the input face of the intensifier 3 and it is paced against this face. In practice, the test chart 6 comprises a grid pattern (FIG. 2) of horizontal and vertical bars. In a preferred example, the test chart has a round external shape, with a diameter of about 30 cm., and has bars spaced out from one another by about one centimeter and having a width of the order of 1 mm.

Figure 3:
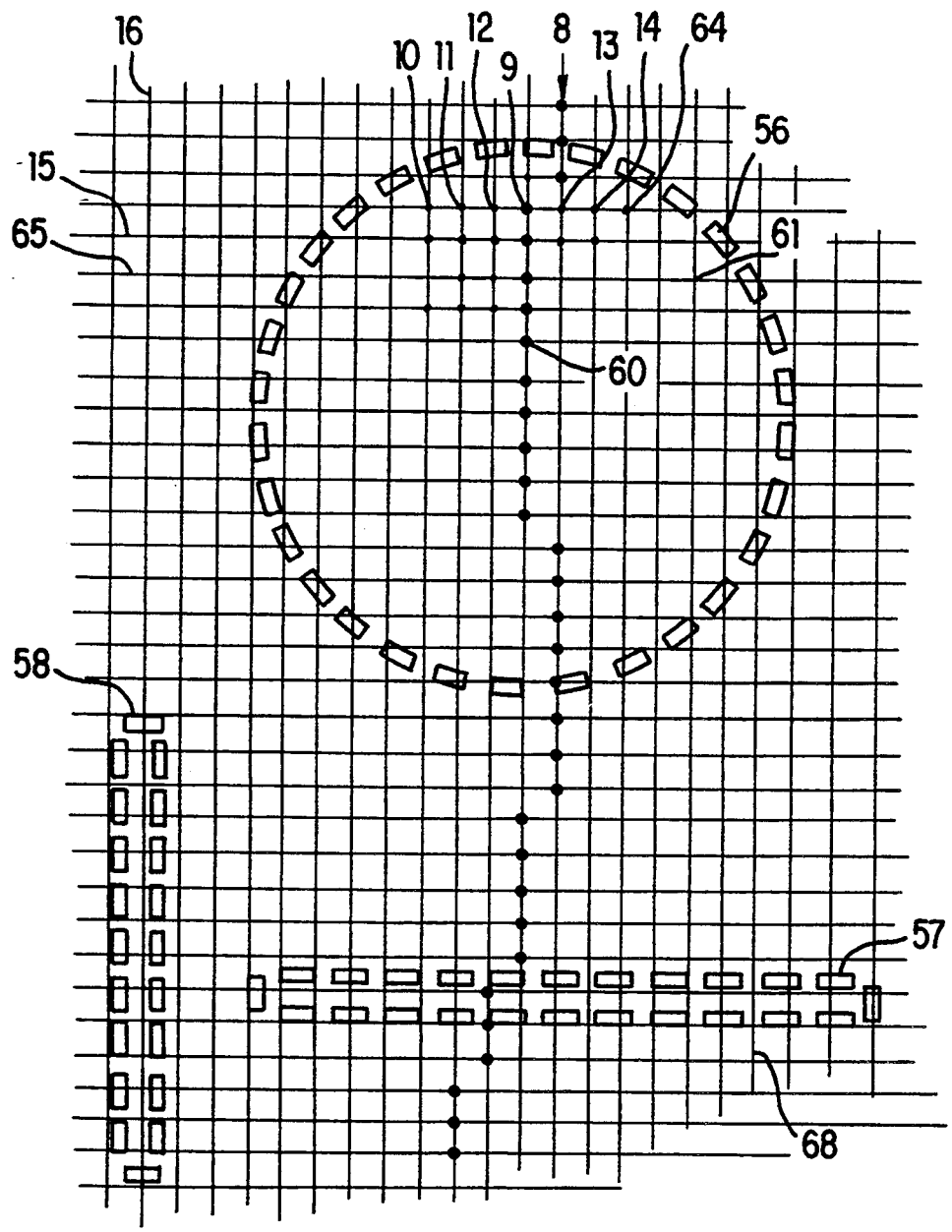
FIG. 3 shows a graphic representation of operations of mathematical morphology, enabling the automatic detection of the image of the test chart.

During a distortion measuring operation, an image resembling that of FIG. 3 is recorded in the image memory of the device 4, and it can be displayed on the screen of the monitor 5. This image comprises a collection of addresses of memory cells, corresponding to the image elements or pixels of the image displayed, associated with information elements representing the grey level. These grey levels can be displayed by the spot of the monitor, on the screen of this monitor, and in the last analysis they correspond to the luminosity assigned to these image elements. The bars of the test chart, in this case for example a bar 8, are distorted (exaggeratedly herein).

It is seen that, in addition to the distorted geometrical character of the image of the bar 8, this bar is represented by pixels having a high grey level, for example the pixel 9, and by pixels having a low grey level, for example the pixels 10 to 14. The latter pixels are depicted by small dots, as opposed to the big dots substantially showing the center of the bar 8 at the position of a profile 15 perpendicularly intersecting the bar 8. On either side of the position of the pixels 10 and 14, which have a low grey level, the image memory has image elements with a grey level that is almost zero (but for the noise). This is shown schematically by the absence of dots at the intersection of the lines 16 and 15, symbolizing x-axis and y-axis values (addresses) of image elements.

Figure 4:
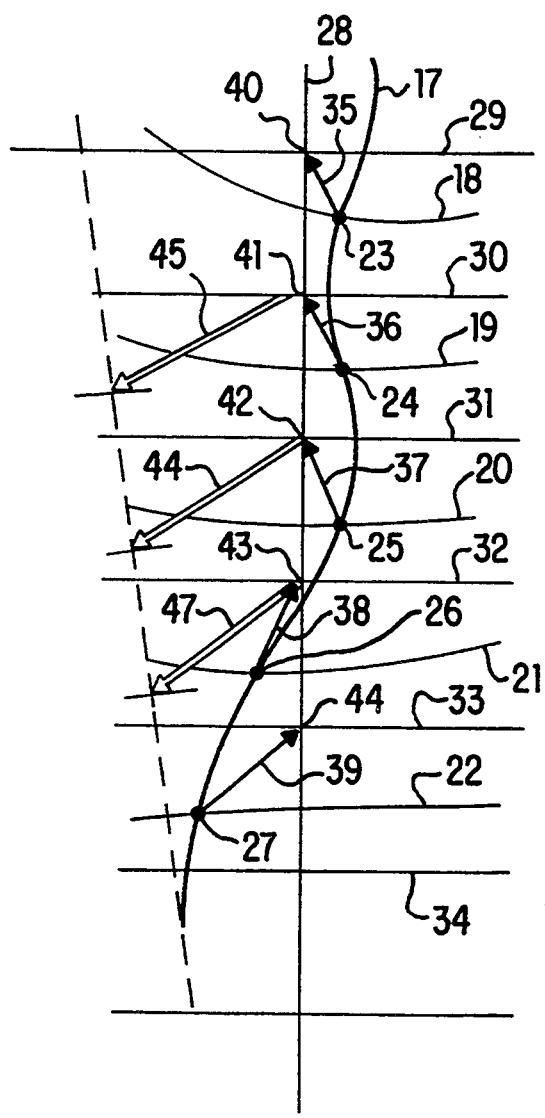
FIG. 4 shows the schematic drawing of the corrections of distortion to be applied to restore the images geometrically.

FIG. 4 shows, in substance, the main principle of the invention. As shall be seen hereinafter, it will be possible to make a very precise computation of the coordinates, namely the addresses, of all the image elements representing the centers of the horizontal and vertical bars 17 to 22 respectively of the test chart. It will also be shown that it is possible to make an automatic computation of the addresses of the points of intersection 23 to 27 of all the bars with one another. Assuming that the test chart occupies a position known in advance, represented for example by the bars 28 to 34, it becomes possible to compute the shifts δ, 35 to 39 respectively, to be assigned to the coordinates of the real image elements that may be located respectively at 23 to 27, to bring them to locations 40 to 44, where the geometrical distortion may be considered to have been eliminated.

For real image elements located at an intermediate position between elements such as 23 to 27, a corrective bilinear interpolation is proposed so as to assign them a shift 5 that takes account of their immediate surroundings.

An objection may be raised that the position of the test chart 6 on the intensifier 6 is not known, and that ultimately there is no exact knowledge of the positions of the theoretical images 28 to 34 of these bars nor that of their intersections. However, it may be noted that the grid itself is known. If we then make the additional assumption that the test chart 6 is provided with bars distributed in a particular way, for example regularly, it may be assumed that the shifts δ 35 to 39 are known, firstly to within plus or minus one whole shift of the pitch of the grid and, secondly, to within plus or minus one change of axis. This change of axis takes account of the real orientation of the axes of the test chart in relation to the directions that are arbitrarily assigned to them in the image memory. It will then be noted that these two approximations are not a source of trouble since they affect all the image elements either in the same way or coherently. Indeed, the same translation by a whole number of pitches of the grid and the effects of one and the same change of axes would have to be applied to all the theoretical intersections 40 to 44.

In FIG. 4, a line of dashes shows, for example, the non-distorted and real position that should be occupied by the theoretical axes 28 to 29, representing the virtual image of the test chart. All the translations and changes in axes are represented by the double arrows 45 to 47. It is seen that these double arrows do not necessarily all have the same length. This ultimately means that the test chart 6 need not necessarily have been placed in such a way that its different bars are subsequently strictly parallel to image lines and columns of the image memory or of the image displayed.

However, it is important to note that if we take the precaution of acquiring all the positions of the X-ray tube 1/intensifier 3 assembly, with a test chart 6 that is held on the tube 3 is a fixed position that is constant during the various acquisitions, the effects of these translations (and changes of axes) 45 to 47 will be the same in all the image. In the ultimate analysis, the way in which the test chart has been placed on the intensifier 3 during these acquisitions of corrections will have no influence.

Figure 5:
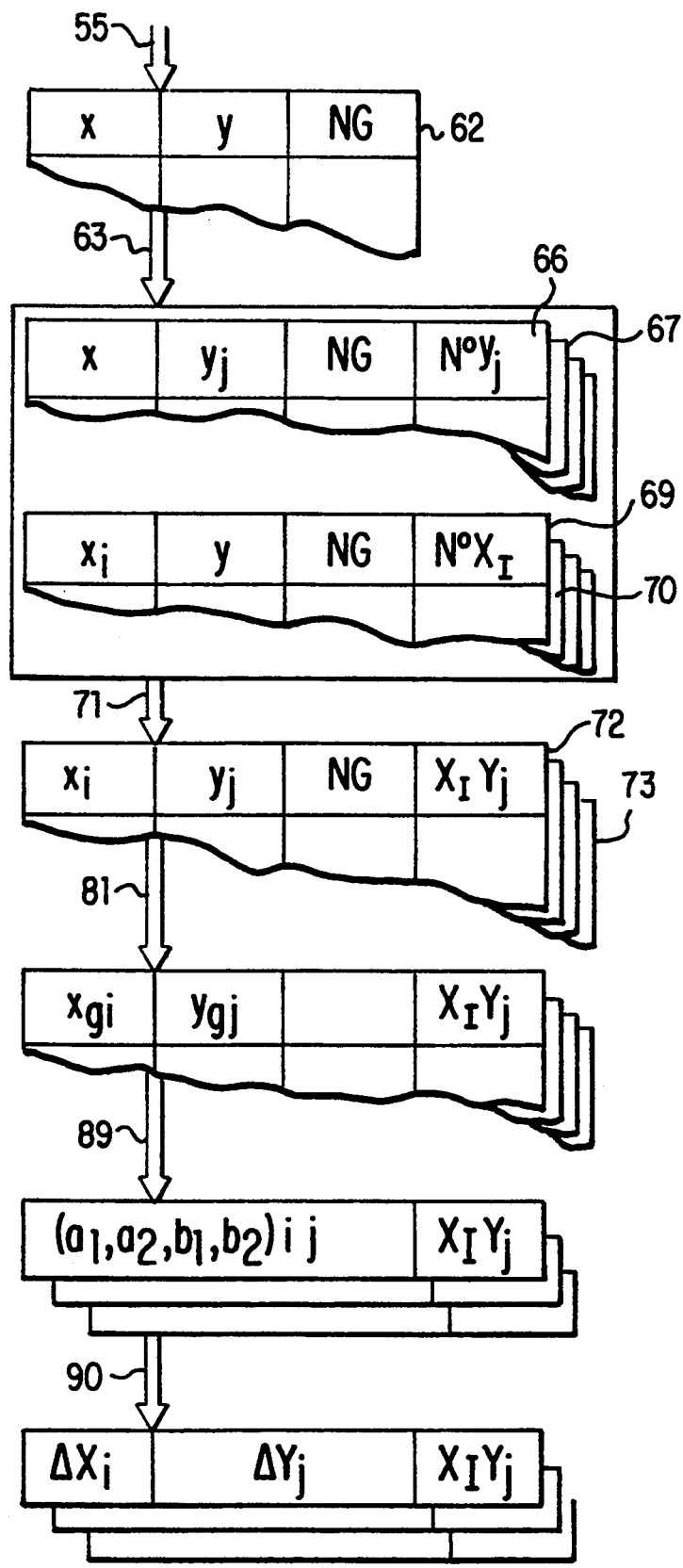
FIG. 5 shows the sequence of the preferred operations implemented in the process of the invention.
Figure 6:
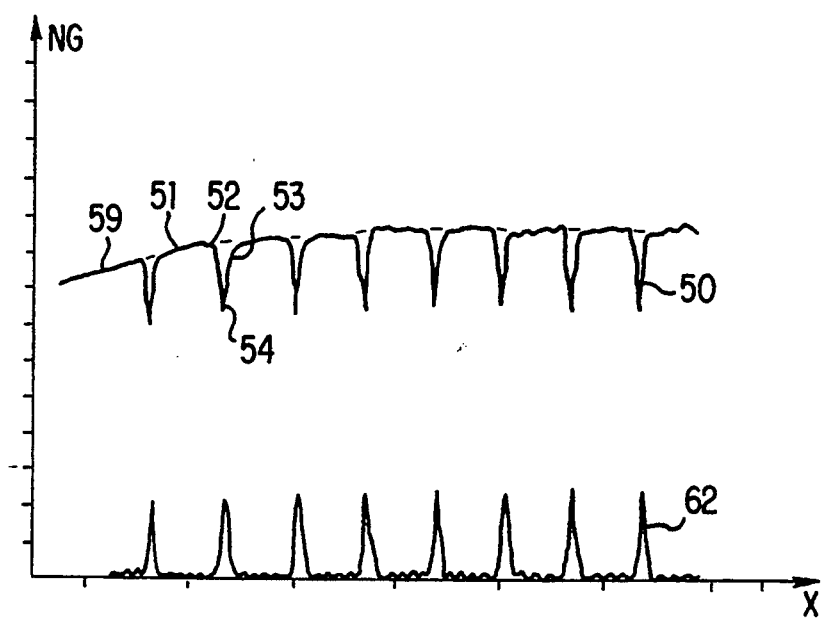
FIG. 6 shows the effects of a particular processing of the images to render the background stationary and remove background noises.

FIG. 5 gives a schematic view of all the steps of the process of the invention. This shall be explained with reference to FIGS. 6 and 3 which correspond to bars in the digital image contained in the image memory. FIG. 6 shows a line 50 obtained by the exploration of the image memory, for example along a profile such as the profile 15. Addresses (namely image elements) are encountered along this profile. The y-axis value of these addresses is constant, but their x-axis value varies by one unit from one pixel to another, from one image element to another. In first regions 51, the grey level is high. Indeed, in these regions 51, corresponding to inter-bar spaces, the X-radiation has greatly excited the intensifier 3. The corresponding electrical signal detected has been high. By contrast, on either Side, namely 52 and 53, of the middle 54 of the bar, for example the bar 8, there are regions where the grey level falls. These regions correspond to the locations of the pixels 10 to 14. The middle 54 of the bar, for its part, corresponds schematically to the pixel 9.

It will be noted that the signal shows a variation of its component as and when the profile continues to be explored along the x-axis. This development is related to the presence of a non-stationary image background. This background is ultimately a source of difficulty. For this stationary background prevents the implementation of a simple detection threshold to automatically identify the position of the bars along the profiles. In the invention, when it is necessary, during an operation referenced 55 in FIG. 5, the image is made stationary by the application to this image, preferably, of a morphological transformation known as a top hat transformation.

A morphological transformation such as this uses opening and closing type operations that are transformations proper to the theory of mathematical morphology. It will be recalled that a closing operation is constituted by an expansion followed by an erosion. Conversely, an opening is constituted by an erosion followed by an expansion. It will be recalled that an erosion of an image consists in the creation of another image after an exploration in erosion of the basic image. The basic image is explored by means of a window having given dimensions and a given geometrical shape and possessing a given center. For example, in the invention, three preferred types of windows (FIG. 3) are used: firstly, a circular window 56 constituted by a circle with a radius of 5 pixels and, secondly, segment windows, 57 and 58 respectively. The length of these segments is 9 pixels and their width is only one pixel. It is possible to give these segments 57 and 58 as well as the circle 56 a center. This center may be any point of the window. It is preferably a pixel located at the geometrical center.

When the basic image is explored with a window, an assessment is made of the grey level of all the pixels of this image located vertically to this window. In a given position of exploration, the grey levels of the pixels vertical to the window may range from $\alpha$, which is a minimum value, and A which is a maximum value. In an erosion operation, it is decided to assign a grey level equal to α to the element of the image to be created that has the same coordinates at the center of the window in the basic image. In an expansion operation, a value A is assigned to the pixel of the image to be created, that has the same coordinates as the pixel vertical to the center of the window. In this case, it is said that the erosions and the expansions are done in terms of grey level. The immediate result thereof is that the opening and closing operations are also done in terms of grey level. By contrast, if the basic images are in binary mode, or even if a threshold is defined, below or above which the grey level is considered to be 0 or 1, the closing and opening operations are done correlatively in binary mode. The geometrical shape of the exploration window is quite related to the result to be achieved.

If it is assumed that it is sought to obtain 512×512 pixel images with an input face of the image intensifier, the diameter of which is typically of the order of 30 cm, it is deduced therefrom that the distance between two neighboring pixels is of the order of 0.5 mm. If, as has just been indicated, a circular window is then chosen, with a diameter of ten pixels (5 mm) whereas the width of the image of the bars, even when distorted, is at any rate smaller than ten pixels, it is possible, with an operation for closing the image, to obtain the contour 59 (FIG. 6). For, during the expansion operation of this closing, A is assigned as the grey level to all the window centers, hence to all the elements of the expanded image. If A varies slightly, the slow variation of A is thus preserved. Ultimately, the continuous component of the background image, which does not include the peaks 54, has been restored. During the next erosion operation of this closing, α is assigned as the grey level to all the elements of the eroded image corresponding to the center of the image in the expanded image obtained beforehand. It could be shown that this closing operation amounts to filtering the peaks 54 in such a way as to leave only the contour 59.

If

CLOSE(I)

designates the expanded and then eroded basic image I, it is realised that the basic image can be subtracted, pixel by pixel, from this expanded-eroded image. We then obtain the contour 62, also shown in FIG. 6, from which the background noise has disappeared. The image 62 is therefore equivalent to the collection (FIG. 5) of the coordinates of the pixels placed in relation to their grey level (NG) and made stationary. Hereinafter in this description, this digitized image made stationary shall be called M.

An operation 63 is then used to make a search, in the image M, for the position of the bars. The search for a bar, when the coordinates of at least one pixel that definitely belongs to a bar have been found, consists in exploring the grey levels of the immediately neighboring pixels to try and determine whether they belong to the same bar. However, this operation is not facilitated when automatic exploration leads to the position of the intersections of the horizontal and vertical bars. Indeed, there is a risk that the automatic exploration process will leave a given type of bar, for example a vertical one, and then start exploring a bar of another given type, for example a horizontal bar. To avert this risk, two images are created out of the image M. A first image includes only the vertical bars, and a second image includes only the horizontal bars. To this end, the image M is made to undergo two opening operations. A first opening operation

OPEN (M, 57)

can be used to give the image of the opening of the image M (erosion followed by expansion) by the segment 57. It is seen that, during the erosion stage corresponding to this opening, all the grey levels of the pixels that are located outside the horizontal bars are cancelled. Indeed, the segment 57 is horizontal and, as soon as this segment no longer directly explores a horizontal bar, it makes a partial exploration of a vertical bar. And at least one of the pixels vertical to this window then possesses a zero or very low grey level. During the expansion operation that follows, the pixels of the vertical bars are not recreated. As a result, the segment 57, during this opening operation, enables the production of an image of the horizontal bars alone. An image of the horizontal or line bars is characterized by the collection of the addresses x, $Y_j$, the associated grey level of which is neither zero nor very low. The same opening operation is redone, but with the segment 58. This time, an image of vertical bars, i.e. columns, is determined, namely the collection of the pixels with coordinates $x_i$, y, the associated grey level of which is not zero.

Ultimately, with these two operations, there is obtained an image of lines or an image of columns in which there is no longer any bridge between the lines or between the columns. FIG. 3 shows this point of view, in which the horizontal bars are no longer shown.

It may be said that, in these images of vertical bars or horizontal bars, we are then dealing with separated sets. In a labelling operation, a column or line number respectively is now assigned to each of these sets. In practice, this number represents the x-axis value or the y-axis value, respectively, of the bar in the virtual image of the test chart. To this end, these column or line images are explored so as to assign a number to each column or each line. A line number will be a number $Y_1$, $Y_2$, or more generally $Y_j$ and this line number will be assigned as an additional dimension to the collection of the pixels, the addresses x, $Y_j$ of which have shown that they belong to one and the same set. For example, to determine the collection of the pixels $X_i$, y belonging to the bar 8, the information content of the pixels belonging to a profile is explored by moving from left to right. The information content of each image element address belonging to this profile is tested.

For example, when the pixel 10 is reached, it is assigned a number. This number will correspond to the number of the bar No. 8. The pixels 11, 12, 9, 13 and 14 are then explored and receive the same number. The pixel 64 receives no number. Its grey level is too low: it does not belong to a bar, and nor do the following pixels until pixels with an information content resembling that of the pixels 9 to 14 are encountered again on the same profile. In this case, they are assigned a column number incremented by one unit. The process is continued in this way until the right-hand lateral edge of the image. The pixels belonging to each column having been thus marked, each of them is then followed upwards and then downwards in going from one pixel to its neighbor with the highest grey level. In this journey, its pixels $X_i$, y are assigned its number $X_i$. Continuing the process in this way, the following are created: the collection 69 of the addresses of the image elements corresponding to the column $Y_I$, the collection 70 of the addresses of the image elements belonging to the column $Y_{I+1}$ and so on and so forth.

This operation can be repeated by the exploration no longer of the vertical bars 15 but of the horizontal bars. We then obtain the collections 66, 67 and the following collections of the addresses of the image elements belonging to lines numbered $Y_J$ or $X_J+1$.

An operation 71 is then used to search for the rough positions of the intersections of the bars. These intersections are represented by the collections of the image elements having addresses $X_i$ and $Y_j$ corresponding respectively to columns $X_I$ and $Y_J$ at the same time. Thus, there are obtained the collections 72 to 73 of pixels assigned to each of the intersections $X_I$, $Y_J$. In practice, the step 71 may be executed at the same time as the pixels of the second group of the bars are determined.

Figure 7A:
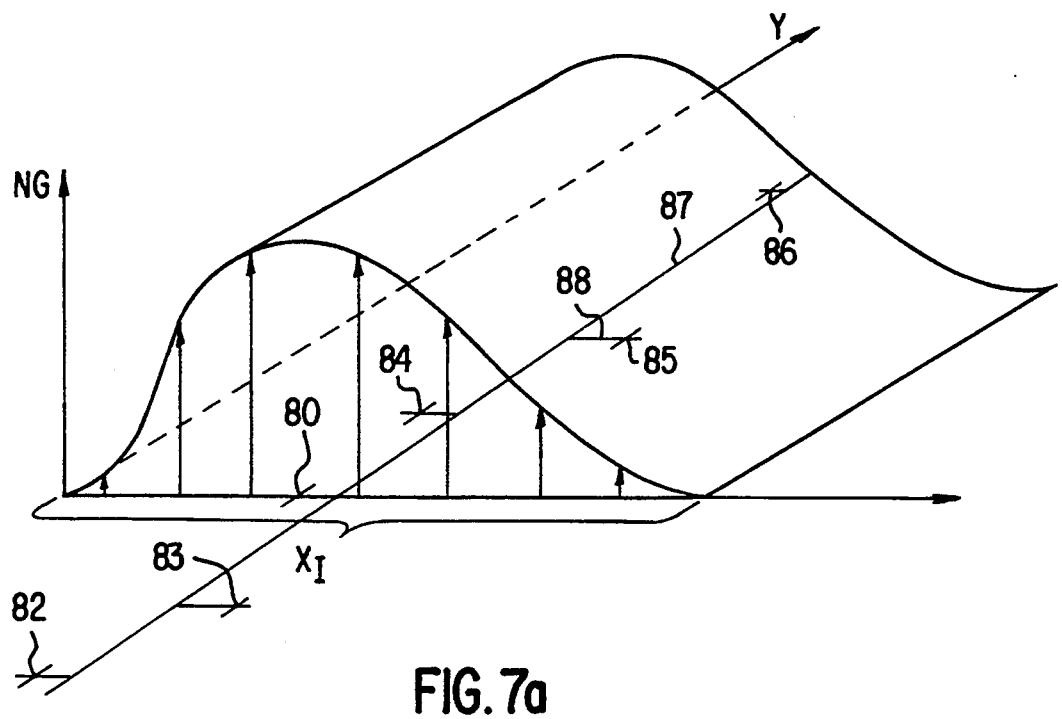
FIGS. 7a and 7b shows the technological characteristics that lead to the determining of the best test chart possible.
Figure 7B:
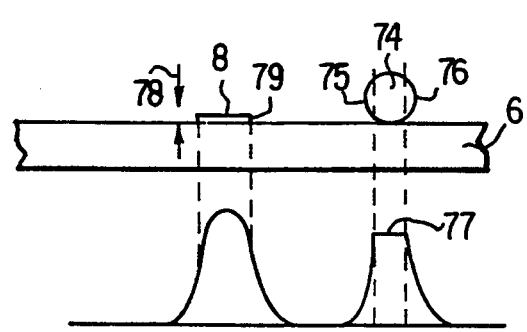

FIGS. 7a and 7b show a specific feature of the test chart enabling a degree of precision in the correction of the distortion to within less than a tenth of a pixel. The test chart 6 (FIG. 7b) could be made by means of an arrangement of absorbent wires 74, for example made of lead or another metal. However, the making of a test chart such as this has two drawbacks. Firstly, on the edges 75 and 76 of the wires, the height crossed by the X-radiation is smaller than the height crossed at the center of these wires. As a consequence, the grey levels detected corresponding to positions vertical to these places crossed are not homogeneous with the grey levels detected vertically to the center of the wires 74. Furthermore, the second drawback is that, if they are be mechanically sturdy, the wires should be made with a certain diameter. As a result, saturation of absorption is swiftly reached. In the end, vertically to the central part of the wire 74, the grey level signal is a flat signal 77. It is not possible, with a flat signal such as this, to know the exact position of the center of the wire 74.

In a preferred embodiment, the test chart is made by the photoetching of a gold layer 78 having a thickness. The thickness of this layer is preferably 0.050 mm. This photoetching is done on a glass plate. The advantage of this approach is that the test chart is almost incapable of being deformed. Furthermore, gold is a material whose use is perfectly mastered in photoetching. The precision that can be obtained in photoetching with gold is of the order of one to five thousandths of a millimeter. Furthermore, gold is also more absorbent than lead and, hence, a thickness of 0.05 mm is sufficient to prompt a non-saturated absorption signal at the commonly used levels of X-ray power. Finally, the photoetching approach can be used to obtain steep flanks 79 of strips 8 constituting the bars of the test chart. In this way, the phenomenon of the gradual change in the grey level of the neighboring pixels represents only the X-ray illumination and not any added parasitic phenomenon. The test chart does not contribute any imprecision of its own.

FIG. 7a gives a view, according to a given profile, of the grey levels measured for neighboring pixels and corresponding to a column numbered $X_I$. In the invention, a search is made for the position of the center of gravity of the X-ray illumination for each profile. The x-axis value $X_{gi}$ of this barycenter is computed on the value of the grey levels $NG_i$ according to the following equation:

$$X_{gi} = \Sigma(X_i \cdot NG_i)/\Sigma(NG_i).$$

This enables the determining, in fractions of pixels, of the x-axis value of the barycenter 80. The same operation (FIG. 5) 81 of searching for the position of the barycenter is done for all the profiles belonging to one and the same collection. Thus, for example, the barycenters 82 to 86 for the column $X_I$ are obtained. Similarly, other barycenters would be obtained for a segment of this line $Y_J$ or, rather, for a segment of this line located on the rough position of the intersection of the bars.

Then, an equation of an $y=ax+b$ type is computed for a straight line, known as a least error squares straight regression line, wherein the sum of the distances such as 88, squared, from this straight line to the barycenters found is as small as possible. These computations are of a known type, and are such that:

$$a = (N\Sigma x_j Y_j - \Sigma x_j \Sigma Y_j)/\sigma$$

$$b = (\Sigma x_j^2 \cdot \Sigma Y_j - \Sigma x_j Y_j \Sigma x_j)/\sigma$$

where N is the number of points of the regression, and where $\sigma$ is given by:

$$\sigma = N\Sigma x_j^2 - (\Sigma x_j)^2.$$

Once the equation of the image 87 of the center of a bar is known, the same operation is recommenced for all the other segments, vertical or horizontal, of the image. The result of these operations 89 is a collection of coefficients ($a_1$, $a_2$, $b_1$, $b_2$) parametrizing segments corresponding to the intersections of the columns $X_I$ and $Y_J$. In a subsequent operation 90, of an analytical type, a computation is made of the coordinates of the points of intersection of the segments 87 which intersect one another. The coordinates of these intersections correspond ultimately to the coordinates 23 to 27 (FIG. 4) of the distorted image of the test chart. These coordinates of intersections are also associated with the pairs of coordinates $X_I$ and $X_J$ of the intersections of the test chart. Now these intersections, given the precision with which the test chart is made, are known in advance. For example, these coordinates are obtained by multiplying the number of the column by the pitch (measured by the test chart) of the test chart at the corresponding position. To simplify matters, it may be said that it is possible to compute the correction vectors such as 35 to 39 by deducting the values $X_i$ and $Y_J$ from the computed values of the coordinates of the points of intersection of the bars of the test chart.

The correction of the geometrical deformations of the images is then undertaken preferably by bilinear interpolation. A bilinear correction consists in computing the correction of distortion to be assigned to a pixel identified in a 2D mesh as a function of the corrections of distortion to be applied to each of the vertices of the mesh. The corrections of the vertices are combined with one another by means of a weighting that takes account of the relative distance of the pixel from each of the vertices. It will be noted, however, that since the corrections of distortion of the vertices of the meshes of the test chart are given in fractions of a pixel, it is most often the case that the corrected coordinates of the pixels of the acquired image also fall between four pixels. This pixel can then be made to undergo a grey correction. This restoring is done by means of a second bilinear correction in taking account of four corrected pixels that surround a pixel of the image to be displayed.

We claim:

1. A process for the correction of the distortion of radiological images acquired with a luminance intensifier tube, said images comprising a collection of addresses of image elements in relation with grey levels assigned to said elements, said process comprising:

acquiring a real image of a test chart, formed by horizontal and vertical bars, said this test chart being placed in front of the input face of said tube, assessing the distortion of said test chart with respect to its expected theoretical shape, and correcting said radiological images as a function of said assessment, wherein said assessing step includes automatically detecting the position of control pixels by searching, by operations of mathematical morphology, for the positions of bars of each of two types, following and labelling said bars, and localizing and labelling points of intersection of said bars of said two types, and assessing localized shifts of said points of intersection.

2. A process according to claim 1, wherein operations of mathematical morphology are carried out in terms of grey level.

3. A process according to claim 1 or claim 2 wherein said searching step comprises making the background of the image stationary by an operation of mathematical morphology.

4. A process according to claim 1, wherein said searching step comprises creating images of bars of each of said two types.

5. A process according to claim 1, wherein said step of assessing said shifts comprises estimating the position of a control pixel in the image by the intersection of two selected straight segments each belonging to a selected bar in the vicinity of said control pixel.

6. A process according to claim 5, further comprising selecting said segments, said selecting step including computing, along said selected bar, and for image elements aligned along a profile perpendicular to said selected bar, the position of barycenters in terms of grey level, and approximating the position of all the barycenters by a segment from which the sum of the distances to barycenters squared is the lowest.

7. A process according to claim 1 wherein said correcting step comprises computing, by bilinear interpolation between four estimated control pixels surrounding any pixel, the shifts of coordinates to be assigned to said pixel.

8. A process according to claim 1, wherein said correcting step further comprises restoring the grey level of an image element by bilinear interpolation on a neighborhood of four neighboring image elements.

9. A process according to claim 1, further comprising reiterating said process for various positions of the tube in the space of the screen while leaving the test chart in the same place on said tube.

10. A process according to claim 1, wherein said test chart comprises a substrate on which a layer of gold is photo-etched, said gold layer having a thickness of about 50 micrometers.

11. A process according to claim 1, wherein said test chart comprises a regular grid pattern of bars formed from etched metal strips having a width of about one millimeter and being spaced from one another by a distance of about 10 millimeters.

12. A process according to claim 1, further comprising the step of displaying the corrected radiological images.

13. A process for the correction of the distortion of radiological images acquired with a luminance intensifier tube, said images comprising a collection of addresses of image elements in relation with grey levels assigned to said image elements, said process comprising:

(A) acquiring a real image of a movable test chart placed in front of an input face of said intensifier tube, said test chart comprising a substrate on which is photo-etched a metal layer, said test chart having an expected theoretical shape;

(B) assessing the distortion of said real image of said test chart with respect to said expected theoretical shape; and (C) correcting said radiological images as a function of said assessment.

14. A process according to claim 13, wherein said test chart comprises a substrate on which a layer of gold is photo-etched, said gold layer having a thickness of about 50 micrometers.

15. A process according to claim 13, wherein said test chart comprises a regular grid pattern of bars formed from etched metal strips having a width of about one millimeter and being spaced from one another by a distance of about 10 millimeters.

16. A process according to claim 13, wherein said test chart includes a plurality of bars, and wherein said assessing step comprises (1) searching, using mathematical morphology, for the positions of bars of each of two types;

(2) following and labelling the two types of bars located in said step (1); and (3) localizing and labelling points of intersection of bars of said two types; and (4) assessing localized shifts of said points of intersection.

17. A process according to claim 13, further comprising the step of displaying the corrected radiological images.

18. A process for the correction of the distortion of radiological images acquired with a luminance intensifier tube, said images comprising a collection of addresses of image elements in relation with grey levels assigned to said image elements, said process comprising:

(A) acquiring a real image of a movable test chart placed in front of an input face of said intensifier tube, said test chart comprising a substrate on which is photo-etched a layer of gold having a thickness of about 50 micrometers, said test chart having an expected theoretical shape;

(B) assessing the distortion of said real image of said test chart with respect to said expected theoretical shape; and (C) correcting said radiological images as a function of said assessment; wherein said assessing step includes (1) searching, using mathematical morphology, for the positions of bars of said test chart of each of two types;

(2) following and labelling the two types of bars located in said step (1); and (3) localizing and labelling points of intersection of bars of said two types; and (4) assessing localized shifts of said points of intersection, said step of assessing said localized shifts including estimating the position of a control pixel in the image by locating the intersection of two selected straight segments each belonging to a selected bar in the vicinity of said control pixel; and (D) displaying said corrected radiological images.

19. A process according to claim 18, further comprising selecting said segments, said selecting step including (1) computing, along said selected bar, and for image elements aligned with a profile perpendicular to said selected bar, the positions of barycenters in terms of grey level, and (2) approximating the position of all of said barycenters by computing a segment the sum of the square of the distances from the barycenters to which is the lowest.

20. A process as defined in claim 18, wherein said correcting step further comprises restoring the grey level of an image element by bilinear interpolation on a neighborhood of four neighboring image elements.

* * * * *